(12) United States Patent
Berke

(10) Patent No.: US 7,621,897 B1
(45) Date of Patent: Nov. 24, 2009

(54) OPHTHALMIC FLUID APPLICATOR AND METHOD

(76) Inventor: Joseph J. Berke, 3248 Interlaken, West Bloomfield, MI (US) 48323

(*) Notice: Subject to any disclaimer, the term of this patent is extended or adjusted under 35 U.S.C. 154(b) by 340 days.

(21) Appl. No.: 11/293,773

(22) Filed: Dec. 5, 2005

(51) Int. Cl.
*A61M 35/00* (2006.01)
*A61H 33/04* (2006.01)

(52) U.S. Cl. ............ 604/295; 604/294; 604/300; 604/301

(58) Field of Classification Search ........ 604/295, 604/294, 298, 300, 301
See application file for complete search history.

(56) References Cited

U.S. PATENT DOCUMENTS

| | | | | |
|---|---|---|---|---|
| 3,261,355 | A * | 7/1966 | Burbig | 604/296 |
| 6,540,726 | B1 * | 4/2003 | Follman et al. | 604/294 |
| 2006/0129113 | A1 * | 6/2006 | Merrick | 604/294 |

* cited by examiner

*Primary Examiner*—Jacqueline F. Stephens
(74) *Attorney, Agent, or Firm*—Alex Rhodes

(57) ABSTRACT

The combination of a squeezable bottle containing an ophthalmic fluid and a detachable applicator apparatus for efficiently spraying the ophthalmic fluid to an eye. The applicator apparatus includes a body having an inlet end portion for attaching the applicator apparatus to the bottle and an outlet end portion for centering the applicator apparatus on the eye, a circular outer planar flange portion extending outwardly in covering relationship from said body circular outlet portion to limit the intrusion of the outlet end portion into the bony orbital ocular opening which surrounds the eye; and a soft resilient seal for sealing a nozzle when the applicator apparatus is not used. The method comprises the steps of removing a cap from a storage bottle; discarding the cap, adding a nozzle to an outlet of the storage bottle, attaching an applicator to the storage bottle; opening an eyelid to spray a small portion of the ophthalmic fluid from the storage bottle on to the eye; inserting a cylindrical outlet end of the applicator body into the bony orbital ocular opening which surrounds the person's eye to center the discharge nozzle on the eye; squeezing the storage bottle to spray a small portion of the ophthalmic fluid on the eye; and attaching a cap to the applicator to seal the storage bottle and prevent the contamination of the storage bottle.

9 Claims, 5 Drawing Sheets

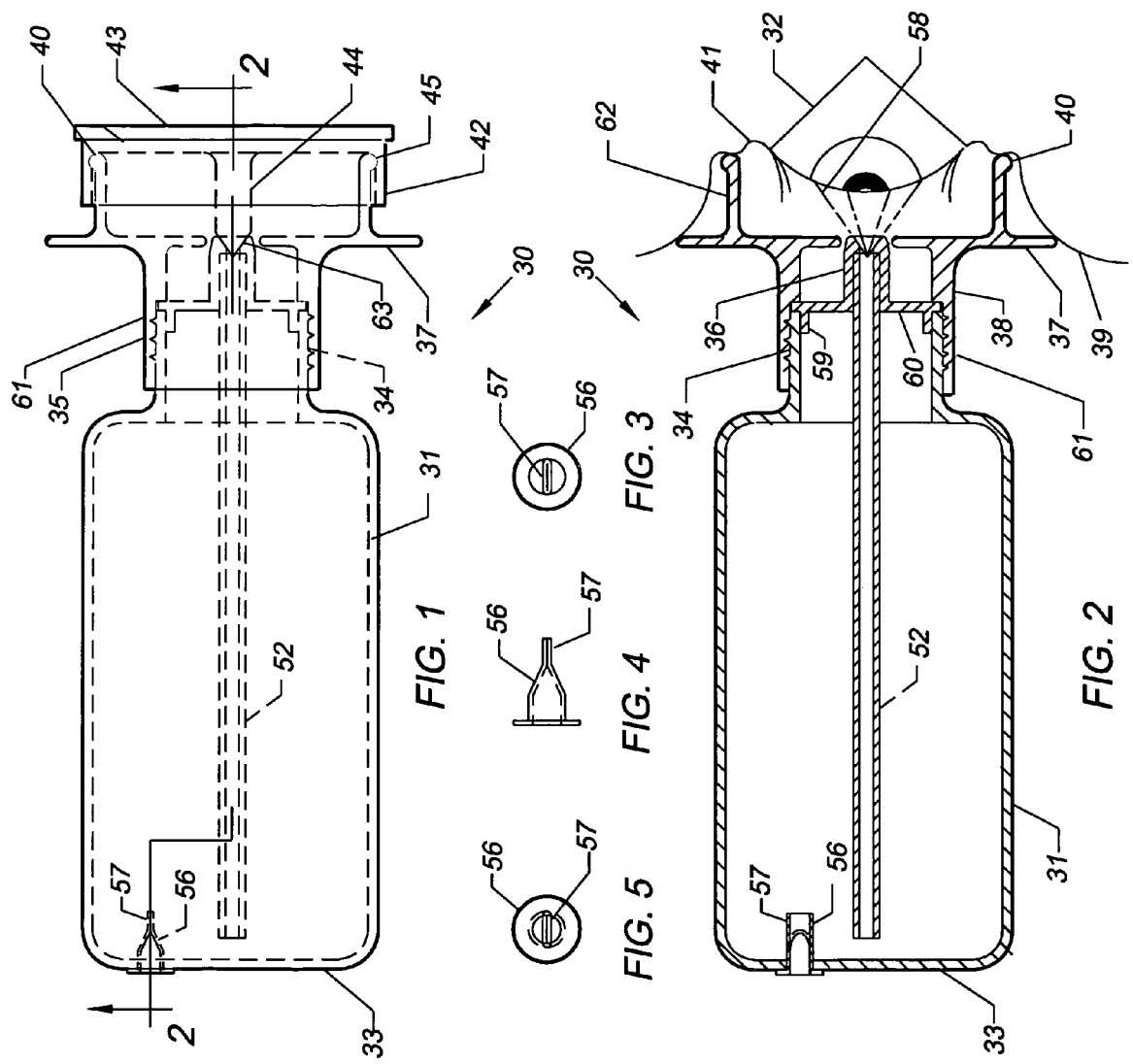

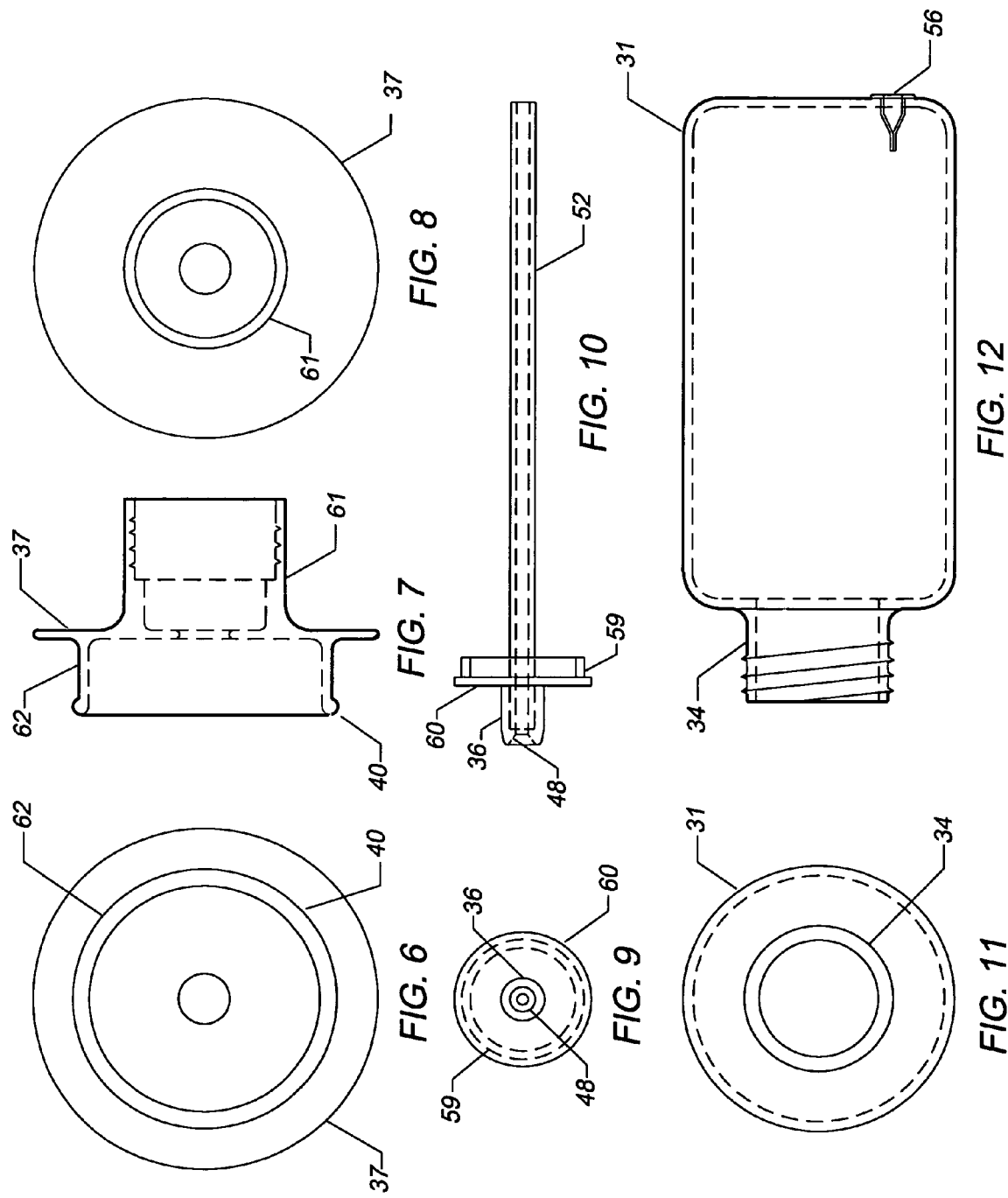

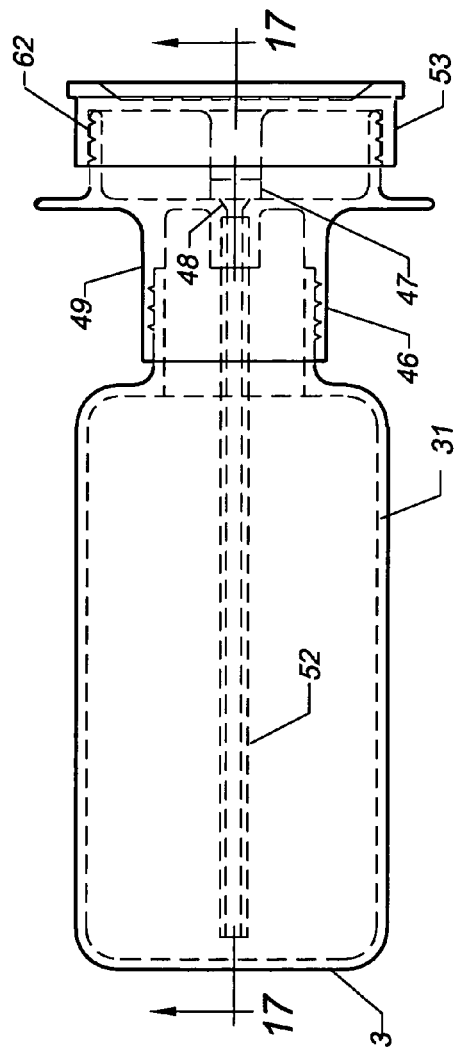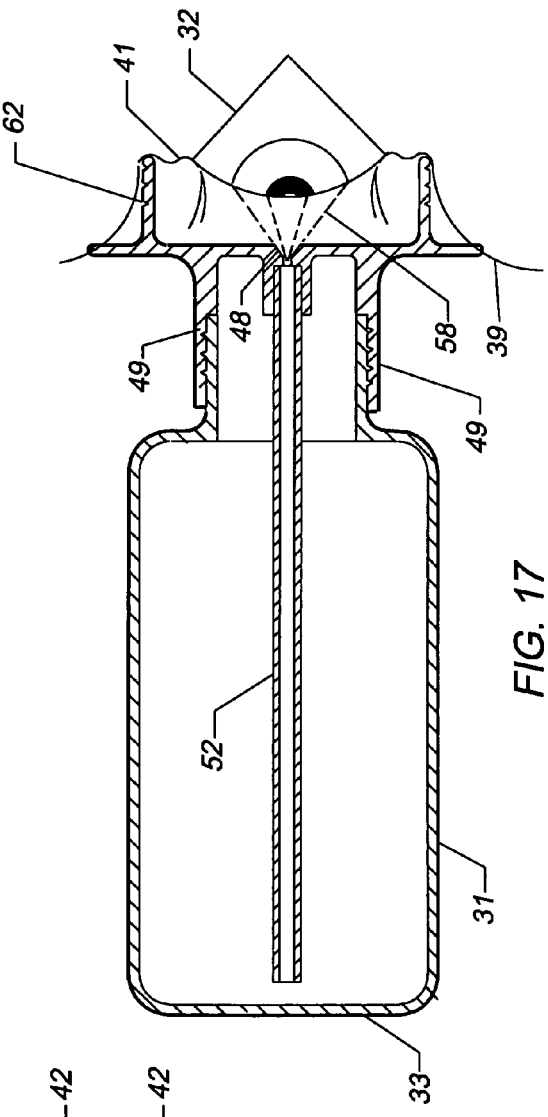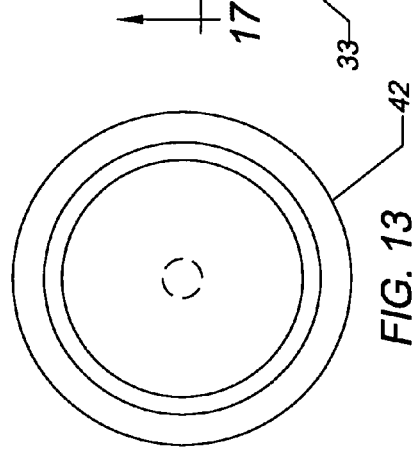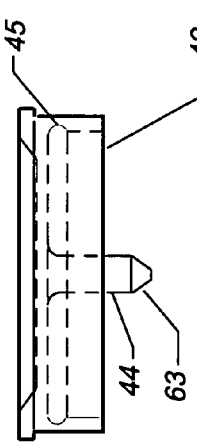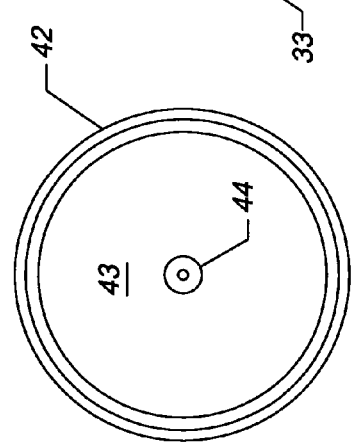

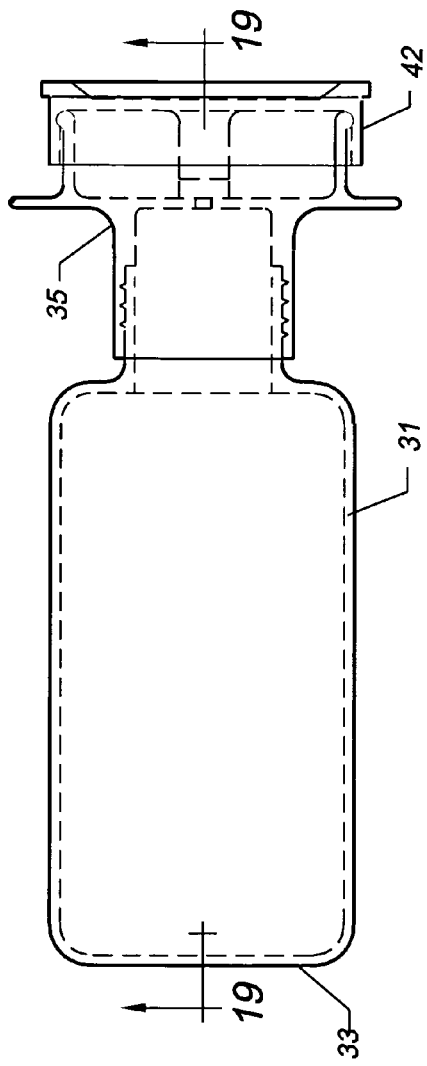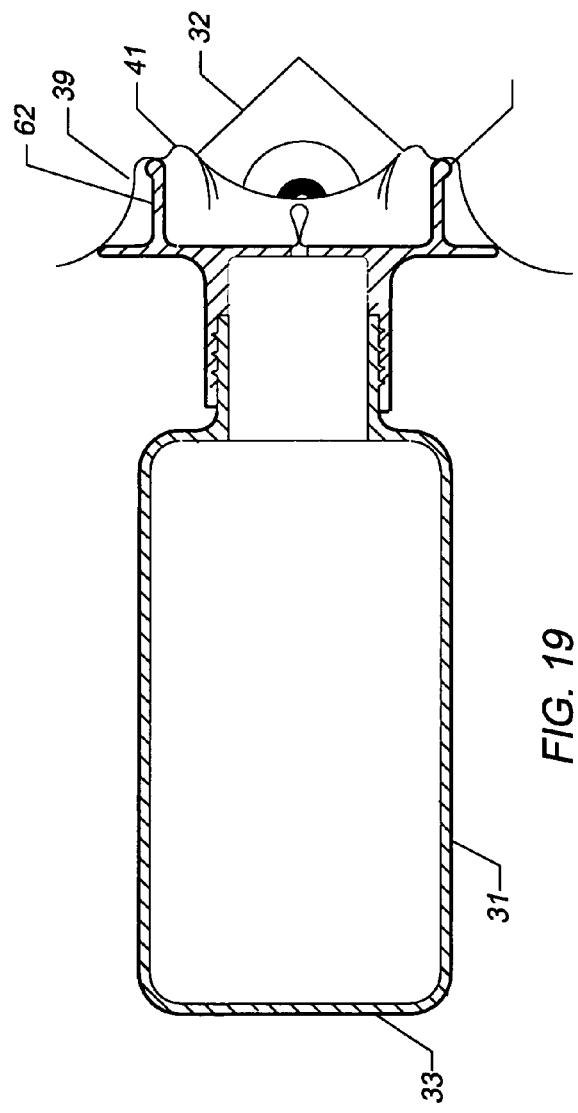

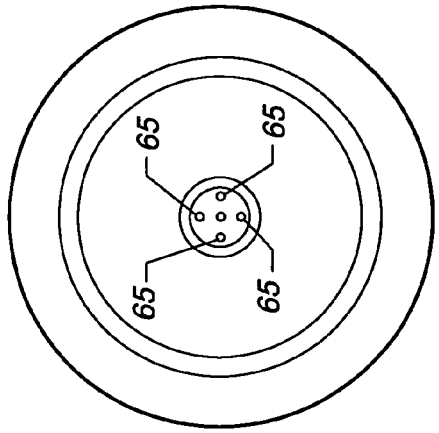
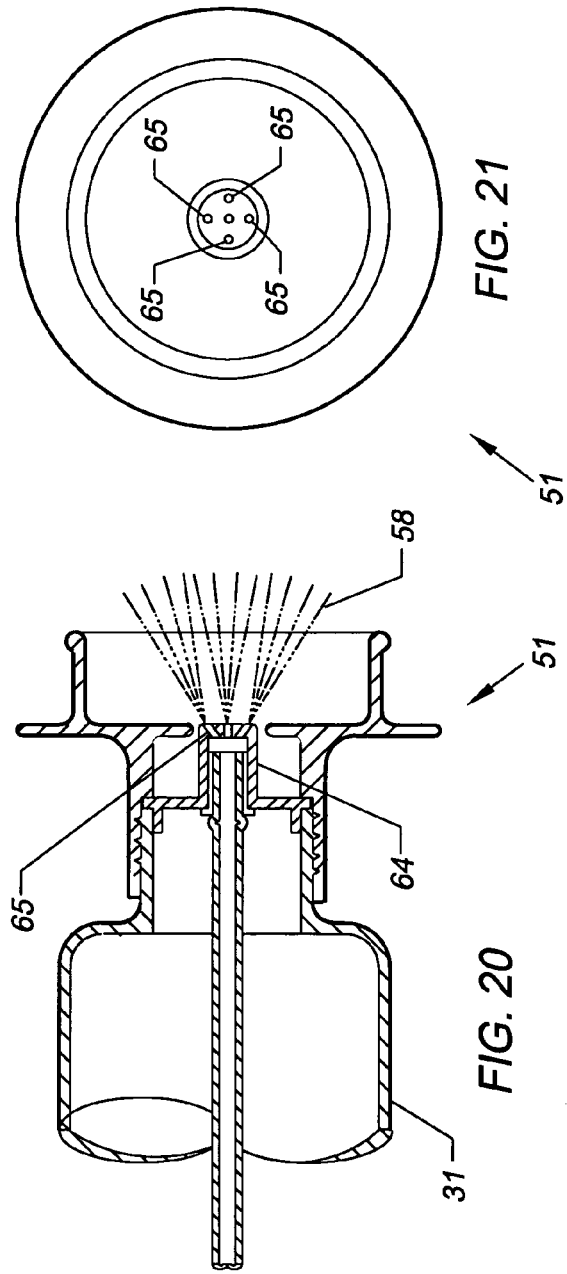
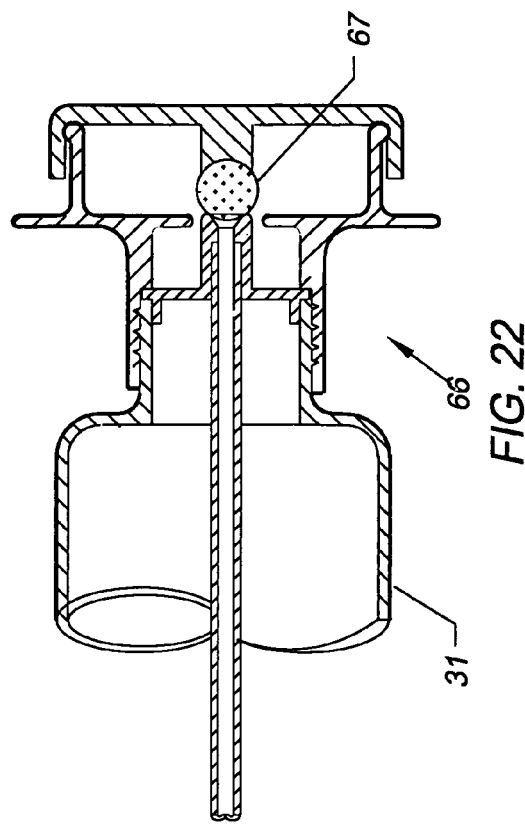

OPHTHALMIC FLUID APPLICATOR AND METHOD

FIELD OF THE INVENTION

This invention relates to fluid dispensing and more particularly to an apparatus and method for administering an ophthalmic fluid from a storage bottle.

BACKGROUND OF THE INVENTION

Ophthalmic fluids are used to moisten the eyes of contact lens wearers, in pre and post ocular surgeries and to treat eye diseases such as glaucoma, bacterial infections and conjunctivitis. The fluids are sold in small bottles and are applied as drops or sprays. The small bottles are similar in shape and size and sealed with threaded closures. The current procedures for administering ophthalmic fluids are somewhat imprecise and the results vary with individuals. With an aging and infirm adult population, the problems with administering ophthalmic fluids have become increasingly problematic.

One problem with current practices is that there is no precise procedure for applying an ophthalmic fluid to an eye. Consequently, expensive ophthalmic fluids are often wasted. The waste needlessly increases medical costs which are already a national problem. Moreover, insufficient doses of ophthalmic fluids are often administered, thereby reducing their effectiveness. Another problem is that excess amounts of ophthalmic fluids fail to enter eyes and often stain clothing. Another problem is that storage bottle outlets and eye droppers are exposed to contamination.

In my U.S. Pat. No. 6,569,131, which is incorporated herein by reference, a spray apparatus is disclosed for applying an ophthalmic fluid to an eye. The spray apparatus prevents an eyelid from closing and directs the ophthalmic fluid on to the eye.

SUMMARY OF THE INVENTION

This invention is an improvement of U.S. Pat. No. 6,569,131. One benefit of the invention is that it can be used with existing ophthalmic fluid bottles. Another benefit is that it prevents an eyelid from closing after the eyelid has been retracted by a person. Another benefit is that it eliminates contamination of bottles and eye droppers by avoiding hand contact with the outlets of the bottles and eye droppers.

One object of the invention is to prevent an eyelid from blinking or closing while administering ophthalmic fluids. Another object, in addition to the foregoing object, is to precisely target an ophthalmic fluid on to an eye. A still further object is to provide an applicator which can be used with existing ophthalmic fluid bottles. A still further object is to reduce the waste of expensive ophthalmic fluids.

In a first aspect of the invention, the applicator has a generally cylindrical body with a threaded end portion for attaching a storage bottle; a diverging orifice for spraying an ophthalmic fluid on to an eye; a cylindrical outlet end portion for preventing the eyelid from closing and for centering the applicator on an eye; a circular flange portion for limiting the intrusion of the applicator into an orbital socket of the eye; and a cap for sealing the bottle when the applicator is not in use. In a second aspect of the invention, the diverging orifice of the first embodiment is replaced with an orifice for applying drops to an eye.

In employing the teaching of the present invention, a plurality of alternate constructions can be provided to achieve the desired results and capabilities. In this disclosure, some alternate constructions are discussed. However, these embodiments are intended as examples and should not be considered as limiting the scope of my invention.

The foregoing features, benefits, objects and best mode of practicing the invention and additional benefits and objects will become apparent from the ensuing detailed description of a preferred embodiment and the subject matter in which exclusive property rights are claimed is set forth in the numbered claims which are appended to the detailed description of the preferred embodiment.

BRIEF DESCRIPTION OF THE DRAWINGS

The invention will be better understood and further objects, characterizing features, details and advantages thereof will appear more clearly with reference to the diagrammatic drawings illustrating a presently preferred specific embodiment of the invention by way of non-limiting example only.

FIG. 1 is a side view of an ophthalmic fluid storage bottle, applicator, valve and cap.

FIG. 2 is a partial cross-sectional view taken on the line 2-2 in FIG. 1.

FIG. 3 is an enlarged rear view of the valve in FIG. 1.

FIG. 4 is a side view of the valve.

FIG. 5 is a front view of the valve.

FIG. 6 is a front view of an applicator body.

FIG. 7 is a side view of the applicator body.

FIG. 8 is a rear view of the applicator body.

FIG. 9 is a front view of a spray nozzle and tube assembly.

FIG. 10 is a side view of the spray nozzle and tube assembly.

FIG. 11 is a front view of an ophthalmic fluid storage bottle.

FIG. 12 is a side view of the ophthalmic fluid storage bottle.

FIG. 13 is a front view of a cap.

FIG. 14 is a side view of the cap.

FIG. 15 is a rear view of the cap.

FIG. 16 is a side view of an alternate embodiment of my invention.

FIG. 17 is a cross-sectional view taken on the line 17-17 in FIG. 16.

FIG. 18 is a side view of a second alternate embodiment of my invention.

FIG. 19 is a partial cross-sectional view taken on the line of FIGS. 19-19 in FIG. 18.

FIG. 20 is a broken longitudinal cross-section of another embodiment of my invention FIG. 21 is a left side view of the embodiment shown in FIG. 20.

FIG. 22 is a broken longitudinal cross-section of another embodiment of my invention.

DETAILED DESCRIPTION OF A PREFERRED EMBODIMENT

Referring now to the drawings wherein like numerals designate like and similar parts throughout the several views, in FIGS. 1 through 15, inclusive, an applicator 30 and a bottle 31 are shown for administering an ophthalmic fluid to an eye 32. One benefit of the invention is that the bottle 31 can an existing ophthalmic fluid bottle 31. Another benefit is that it provides a precise method for targeting an ophthalmic fluid to an eye. A further benefit is that it is easy to use. This is particularly important with elderly patients who often have poor eyesight and poor motor control. A further benefit is that it reduces the waste of expensive ophthalmic fluids. A further benefit is that it insures that a sufficient amount of an ophthalmic fluid will be applied to an eye.

The bottle 31 is a conventional squeeze-type plastic bottle 31 with a flat lower portion 33 and a smaller diameter cylindrical outlet portion 34 for receiving a usual type threaded sealing cap (not shown). In the flat lower portion 33 there is an optional "duck bill" vent valve 56 made of a rubber-like material. A flat forward portion 57 of the valve 56 opens if there is a negative pressure in the bottle 31 to admit air into the bottle.

The applicator 30 may be sold separately or supplied attached to the bottle 31. Attached to the bottle 31 is a spray nozzle 36 for spraying an ophthalmic fluid 58 on to an eye 32. At an end portion of the spray nozzle there is a diverging orifice 48. The spray nozzle 36 is mounted in the outlet portion 34 of the bottle 31 and includes a pick-up tube 52. The spray nozzle 36 and pick-up tube 52 are removable for filling the bottle 31 with the ophthalmic fluid 58. The pick-up tube 52 extends from the spray nozzle 36 to the flat lower portion 33 of the bottle 31. There is a small gap between the pick-up tube 52 and the bottle 36 for admitting the ophthalmic fluid 58 when the bottle 31 is squeezed. As shown in FIGS. 1 and 2, the spray nozzle 36 has a cylindrical portion 59 which is pressed into the bottle's outlet portion 34 and a flange portion 60.

When the applicator 30 is used with an existing bottle 31, a conventional closure (not shown) which is supplied with the bottle 31 is removed and discarded. The cylindrical inlet portion 61 of the applicator 30 threadably engages the existing bottle 31. In the alternative, the inlet portion 61 of the applicator 30 is not threaded and slidably engages the threaded outlet end portion 34 of the bottle 31.

An inlet portion 61 of the applicator 30 extends forwardly to a larger cylindrical outlet portion 62. The inlet portion 61 and outlet portion 62 are separated by bulkhead 37 which extends outward from the applicator to form a circular flange portion, as will be later shown, limits the intrusion of the applicator 30 into the bony skeletal ocular opening 39 which surrounds the eye 32. In the center of the bulkhead there is an aperture which surrounds the nozzle. One benefit of this feature is that the bulkhead 37 act as a shield for preventing the nozzle 36 from injuring the eye 32.

Another feature of my invention is that the cylindrical outlet portion 62 centers the applicator 30 on the eye 32. As shown in FIG. 2, the cylindrical outlet portion 62 has an outer diameter which is slightly smaller than the bony skeletal opening 39 which surrounds the eye 32, allowing the applicator 30 to extend through the skeletal opening 39 to center the applicator 30 with respect to the eye 32. The outlet portion 62 prevents the eyelid 41 from closing. As shown in FIG. 2, end portion 40 of the applicator 30 is spherical to prevent the applicator 30 from scratching the orbital socket 39 of the eye 32.

With reference to FIG. 1, the outwards extending flange portion of the bulkhead 37 bears against the skeletal portion 39 which surrounds the eye 32 to limit the intrusion of the applicator 30 into the eye 32.

The cap 42 seals the applicator 30 and bottle 31 and prevents a loss of the ophthalmic fluid 58 when the applicator 30 is not used. Another benefit is that it prevents contamination of the bottle 31 and applicator 30. The cap 42 consists of a flat circular covering portion 43 and an inward extending cylindrical portion 44. The inward extending cylindrical portion 44 has a tapered end portion 63 which engages the diverging orifice 45 to seal the bottle 31. As shown in FIG. 1, the cap 42 is retained on the applicator 30 an undercut 45 which engages the spherical end portion 40 of the applicator outlet portion 40.

The invention is intended to be used with an existing squeeze-type bottle 31 in the following manner. The cap (not shown) of the bottle 31 is removed and discarded. The applicator 30 and cap 42 are threadably engaged or pressed on to the threaded outlet end portion 34 of the bottle 31. The cap 42 at the outlet end portion 62 of the applicator 30 is removed to expose the spray nozzle 36. An eyelid 41 is manually opened and the outlet end portion 62 of the applicator 30 is inserted into the ocular opening 39 which surrounds the eye 32 to center the applicator 30 and prevent the eyelid 41 from closing. The bottle 31 is squeezed to spray a small amount of the ophthalmic fluid 58 on the eye 32. After the eye 32 has been treated with the ophthalmic fluid 58, the applicator 30 is removed and the cap 42 re-installed to protect the nozzle 36 from contamination and to seal the bottle 31.

Referring now to FIGS. 16 and 17, an alternate embodiment 46 of my invention is shown which is similar to the previously described embodiment. In a first aspect, a cylindrical rubber seal 47 is provided on the cap 42 in lieu of the tapered end portion 63 for sealing the bottle 31. In a second aspect the outlet end portion 62 of the applicator 46 is threaded. The applicator cap 53 threadably engages the outlet end portion 62 of the applicator 46. In a third second aspect, the diverging orifice 48 is an integral portion of the body 49 of the applicator 46.

In FIGS. 18 and 19, an eye dropper embodiment 50 is shown wherein the diverging orifice 48 of the previous embodiments is replaced with an eye dropper orifice 54 and the pick-up tube 52 of the previous embodiments has been deleted.

In FIGS. 20 and 21 an embodiment 51 is shown having a nozzle 64 with small apertures 65 for spraying an ophthalmic fluid 58 on an eye. In FIG. 21 is shown an embodiment 66 with a soft resilient spherical seal 67 for sealing a bottle 31.

From the foregoing it is apparent that my invention is an easy to use apparatus and method for administering an ophthalmic fluid to an eye. It will be further apparent that my invention eliminates the problems which exist with current practices and provides benefits heretofore not available. Although several embodiments have been described it will be observed that the embodiments include the characterizing feature of a cylindrical outlet portion having a diameter which is less that a skeletal opening which surrounds an eye for centering an applicator with respect to an eye and for preventing an open eyelid from closing.

Although only several embodiments have been disclosed, it will be further apparent that other embodiments can be derived by persons skilled in the art by changes such as changes in materials, changes in shape, rearrangements of parts and eliminations of parts without departing from the spirit thereof.

What I claim is new is:

1. In combination with a squeeze-type storage bottle containing an ophthalmic fluid, a spray applicator apparatus for efficiently spraying a portion of said ophthalmic fluid on to an eye, said spray apparatus comprising a body having an axis which is aligned with an axis of said storage bottle and a cylindrical inlet end portion for attaching said apparatus to a cylindrical outlet end portion of said storage bottle; an annular outlet end portion for centering said applicator apparatus on said eye and preventing an eyelid from closing by inserting said circular outlet end portion through a bony ocular opening which surrounds said eye, said annular outlet end portion having an outer diameter that is slightly smaller than said bony ocular opening which surrounds said eye; a small nozzle aligned said axis of said body for spraying a small amount of said ophthalmic fluid on to said eye; a transverse bulkhead which is aligned with an end portion of said nozzle for preventing said nozzle from contacting said eye, said transverse bulkhead extending outwardly across and away from said axis of said body to form an outer planar flange portion for limiting the intrusion of said circular outlet portion into said bony ocular opening; and a re-usable cover for preventing a discharge of fluid from said nozzle and for sealing said body outlet portion when said spray apparatus is not in use.

2. The combination recited in claim 1 further comprising a cylindrical intermediate portion between said inlet portion and said outlet portion.

3. The combination recited in claim 1 wherein said nozzle has a single small diverging orifice for administering said spray on to said eye.

4. The combination recited in claim 3 further comprising a pick-up tube attached to said nozzle.

5. The combination recited in claim 3 wherein said cover for sealing said bottle and covering said body outlet portion is comprised of: a thin circular cover portion for covering said body outlet portion and an elongated downward extending center portion for engaging said diverging orifice to completely prevent fluid from discharging from said nozzle.

6. The combination recited in claim 3 wherein said cover for sealing said bottle and covering said body outlet portion is comprised of a thin circular cover portion for covering said housing outlet portion; a downward extending center portion; and a resilient seal attached to said center portion for sealing said nozzle.

7. The combination recited in claim 1 wherein said housing threadably engages said outlet portion of said squeeze type storage bottle.

8. The combination recited in claim 1 wherein said cover for sealing and covering said storage bottle threaded outlet portion threadably engages said applicator housing outlet portion.

9. The combination recited in claim 1 wherein said cover for sealing said storage bottle and covering said applicator body outlet portion is press fitted on to said applicator body outlet portion.

* * * * *